(12) United States Patent
Pugsley et al.

(10) Patent No.: US 7,416,546 B2
(45) Date of Patent: Aug. 26, 2008

(54) TISSUE PATCHES AND RELATED DELIVERY SYSTEMS AND METHODS

(75) Inventors: Charles H. Pugsley, Pelham, NH (US); Marcia McBride-Sakal, Bolton, MA (US); Kurt Geitz, Sudbury, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 642 days.

(21) Appl. No.: 10/706,965

(22) Filed: Nov. 14, 2003

(65) Prior Publication Data

US 2004/0225247 A1 Nov. 11, 2004

Related U.S. Application Data

(63) Continuation-in-part of application No. 10/428,801, filed on May 5, 2003.

(51) Int. Cl.
*A61M 31/00* (2006.01)
(52) U.S. Cl. ..................................................... 604/500
(58) Field of Classification Search ................. 606/213, 606/151, 154; 424/422, 425–426, 93.1, 93.7, 424/93.2, 443, 447; 604/890.1, 500; 623/14.13, 623/15.11
See application file for complete search history.

(56) References Cited

U.S. PATENT DOCUMENTS

| | | | |
|---|---|---|---|
| 4,458,678 A | 7/1984 | Yannas et al. | |
| 4,687,481 A * | 8/1987 | Nuwayser | 424/449 |
| 4,950,227 A | 8/1990 | Savin et al. | |
| 5,059,211 A | 10/1991 | Stack et al. | |
| 5,122,127 A | 6/1992 | Stanley | |
| 5,182,111 A | 1/1993 | Aebischer et al. | |
| 5,344,454 A * | 9/1994 | Clarke et al. | 623/23.72 |
| 5,429,634 A | 7/1995 | Narciso, Jr. | |
| 5,453,278 A | 9/1995 | Chan et al. | |

(Continued)

FOREIGN PATENT DOCUMENTS

WO  WO 00/74584 A1  12/2000

(Continued)

OTHER PUBLICATIONS

Lambert, Adam, "The Genetically Engineered Biological Bandage: A Functional Proactive Means of Growth Factor Delivery"; The University of Akron, PhD thesis, vol. 5810B of Dissertations Abstracts International, 1997 pp. 1-118.

*Primary Examiner*—Nicholas D. Lucchesi
*Assistant Examiner*—Christopher D Koharski
(74) *Attorney, Agent, or Firm*—Finnegan, Henderson, Farabow, Garrett & Dunner, L.L.P.

(57) ABSTRACT

Endoluminally delivered tissue patches and related systems and methods for delivering the tissue patches for treating lesions of the alimentary tract are disclosed. A tissue patch includes a substrate, a tissue implant attached to the substrate, and a protective liner covering at least a portion of the tissue implant. A method includes providing a tissue patch having a tissue implant attached to a substrate and a protective liner covering at least a portion of the tissue implant. The tissue patch is formed into a contracted state and inserted into a lumen containing the lesion. The tissue patch then is positioned in the vicinity of the lesion. After removing the protective liner to reveal the tissue implant, the tissue implant is placed in the lesion.

13 Claims, 11 Drawing Sheets

U.S. PATENT DOCUMENTS

| | | | |
|---|---|---|---|
| 5,487,889 A * | 1/1996 | Eckert et al. | 424/93.1 |
| 5,502,042 A * | 3/1996 | Gruskin et al. | 514/59 |
| 5,599,788 A | 2/1997 | Purchio et al. | |
| 5,610,241 A | 3/1997 | Lee et al. | |
| 5,637,113 A | 6/1997 | Tartaglia et al. | |
| 5,656,267 A | 8/1997 | Sagen et al. | |
| 5,733,337 A | 3/1998 | Carr, Jr. et al. | |
| 5,766,584 A | 6/1998 | Edelman et al. | |
| 5,782,788 A * | 7/1998 | Widemire | 602/48 |
| 5,842,477 A | 12/1998 | Naughton et al. | |
| 5,868,755 A | 2/1999 | Kanner et al. | |
| 5,893,868 A | 4/1999 | Hanson et al. | |
| 5,910,145 A | 6/1999 | Fischell et al. | |
| 6,001,386 A * | 12/1999 | Ashton et al. | 424/423 |
| 6,090,996 A | 7/2000 | Li | |
| 6,123,667 A | 9/2000 | Poff et al. | |
| 6,129,761 A | 10/2000 | Hubbell | |
| 6,140,452 A | 10/2000 | Felt et al. | |
| 6,149,681 A * | 11/2000 | Houser et al. | 623/1.12 |
| 6,176,874 B1 | 1/2001 | Vacanti et al. | |
| 6,196,965 B1 | 3/2001 | Purdum | |
| 6,540,993 B1 | 4/2003 | Warne et al. | |
| 6,884,428 B2 * | 4/2005 | Binette et al. | 424/422 |
| 6,893,431 B2 * | 5/2005 | Naimark et al. | 604/891.1 |
| 2003/0176827 A1 | 9/2003 | Chandra et al. | |

FOREIGN PATENT DOCUMENTS

| | | | |
|---|---|---|---|
| WO | WO 01/35834 A1 | | 5/2001 |
| WO | WO 02/085402 A1 | | 10/2002 |
| WO | WO02085402 | * | 10/2002 |
| WO | WO 03/094786 A1 | | 11/2003 |

* cited by examiner

TISSUE PATCHES AND RELATED DELIVERY SYSTEMS AND METHODS

This is a continuation-in-part application of application Ser. No. 10/428,801, filed May 5, 2003, which is incorporated herein by reference.

FIELD OF THE INVENTION

The present invention relates to tissue patches and related systems and methods for delivering the tissue patches. In particular, the present invention relates to endoluminally delivered tissue patches for treating, for example, lesions of the alimentary tract to promote healing and reduce risk of infection.

BACKGROUND OF THE INVENTION

Gastroesophageal reflux occurs when stomach acid enters the esophagus. This reflux of acid into the esophagus can occur naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). FIG. 1A schematically illustrates the esophagus as it would appear in a healthy individual in the region of the LES. The LES 1 is a ring of smooth muscle and increased annular thickness existing in approximately the last four centimeters of the esophagus 3. In its resting state, the LES 1 creates a region of high pressure (approximately 15-30 mm Hg above intragastric pressure) at the opening of the esophagus 3 into the stomach 5. This pressure aids in closing the esophagus 3 so that contents of the stomach cannot pass back into the esophagus 3. The LES 1 opens in response to swallowing and peristaltic motion in the esophagus 3, allowing food to pass into the stomach 5. After opening, however, a properly functioning LES 1 should return to the resting, or closed state. Transient relaxations of the LES 1 do occur in healthy individuals, typically resulting in occasional bouts of heartburn. Also, lack of support for the esophagus at the LES or widening of space of the diaphragm that supports the esophagus often allows a portion of the gastric fundus to protrude up through the esophagus, resulting in movement of the LES and changing the pressures seen at the LES region. This condition, generally referred to as hiatal hernias, is common in the elderly and is one of the major contributing factors in GERD.

Referring to FIG. 1A, the stomach lining 2 is comprised of columnar cells, while the esophageal lining 4 is comprised of squamous cells. These cells are histologically distinct from one another and serve vital functions. For example, while columnar cells are acid resistant, squamous cells are prone to damage by stomach acid. The point at which the cell types transition is known as the "Z-line" 6 and is generally located in a healthy individual at a point below the LES region 1. However, when a healthy esophagus is subject to repeated, prolonged exposure to stomach acid reflux, the cell structure of the esophageal lining 4 changes from the normal squamous cells into the columnar cells and, as shown in FIG. 1B, "fingers" 7 of columnar cells appear in the area of the LES 1. The "fingers" 7 of columnar cells, also known as Barrett's Epithelium, can occur in a patient suffering from chronic GERD.

Since an individual with Barrett's epithelial tissue is many times more likely to develop esophageal cancer than a healthy individual, a surgical resection of the tissue or tissue ablation is often performed. This type of surgical resection of diseased tissue, however, introduces widely dispersed, open wounds that are very painful to the patient and take a long time to heal. These wounds may be prone to infection if the acid is not properly managed through appropriate medications. Other types of wounds or lesions may also be introduced during the natural progression of the disease, which are subject to the same harsh condition present in this part of anatomy.

Therefore, it is accordingly an object of the present invention to provide devices and related methods for treating lesions in the alimentary tract, such as, for example, endoscopic mucosal resection (EMR) sites or esophagus. In particular, the devices and methods promote healing of the lesions by stimulating tissues for rapid healing and/or regrowth while reducing the risk of infection and discomfort of the patient in the least invasive way possible.

In order to eliminate or reduce the need for highly invasive and physiologically insulting surgical procedures, endoscopic techniques have been developed for the diagnosis and/or treatment of certain disorders. Endoscopy allows examination and the manipulation of tools and tissues in interior areas of a patient's body utilizing naturally occurring orifices in the body, such as the alimentary tract. Endoscopic surgery eliminates or greatly reduces the need for the large, surgically-produced openings traditionally required to obtain access to sites deep within the body and, thus, reduces the attendant trauma to skin, muscle, and other tissues. Endoscopic surgery also eliminates or greatly reduces various risks associated with effects of anesthesia during a course of surgery. Consequently, a patient may experience less pain, recover more quickly, and present less scarring.

Therefore, it is accordingly another object of the present invention to provide devices and related methods for endoluminal delivery of the treatment device to a lesion of the alimentary tract, which eliminate or reduce the need for highly invasive, physiologically insulting surgical procedures.

SUMMARY OF THE INVENTION

In accordance with the purpose of the invention, as embodied and broadly described herein, one aspect of the invention provides a tissue patch for treatment of a lesion in an alimentary tract of a patient. The tissue patch includes a substrate, a tissue implant attached to the substrate, and a protective liner covering at least a portion of the tissue implant. The tissue implant may be a genetically engineered tissue. The tissue implant may be placed on a surface of the substrate, or be embedded in the substrate in the form of a cellular suspension.

In another aspect, the substrate may be a bio-absorbable gel. The substrate may include a bio-absorbable material having a predetermined thickness designed to last for a predetermined time period required for healing of the lesion so as to protect the tissue implant from conditions in the alimentary tract. The substrate may also include a therapeutic agent selected from a group consisting of human growth hormone, genetically engineered cells, antibiotics, analgesics, and pH sensitive or reactive chemicals. The therapeutic agent may be infused into the substrate, or be layered in a predetermined depth within the substrate so that the therapeutic agent may activate at a predetermined time. The substrate may have a first surface for receiving the tissue implant and a second surface opposite to the first surface for facing a lumen of the alimentary tract. The tissue implant may occupy an area in the first surface of the substrate, where the area may be less than the surface area of the first surface.

According to yet another aspect, the tissue patch may include an adhesive material to hold the patch proximate the lesion. The adhesive material may include cyano-acrylate. The protective liner may be attached to the substrate via the adhesive material. The adhesive material for attaching the protective liner may occupy at least a portion of the first surface other than the area occupied by the tissue implant.

In still another aspect, the protective liner may be removably attached to the tissue patch. For example, the protective liner may be configured to be peeled away from the tissue patch. Alternatively, the protective liner may be removably attached to the substrate.

According to still another aspect, the tissue patch may be configured to be delivered endoluminally. The tissue patch may be configured to be folded into a contracted state during delivery into the lesion. For example, the patch may be configured to be rolled into a cylindrical shape. The tissue patch may also be capable of expanding upon deployment into the lesion. The tissue patch may include a carrier attached to the substrate, which may be configured to peel away from the substrate.

According to another aspect of the present invention, a method of treating a lesion in a lumen of patient's body is provided. The method may include providing a tissue patch having a tissue implant attached to a substrate and a protective liner covering at least a portion of the tissue implant, forming the tissue patch into a contracted state, inserting the tissue patch in the contracted state into a lumen containing the lesion, positioning the tissue patch in the vicinity of the lesion, removing the protective liner to reveal the tissue implant, and placing the tissue implant in the lesion.

In another aspect, the method may also include placing the tissue patch on a portion of a catheter for inserting the tissue patch in the contracted state. The method may also include expanding the tissue patch from the contracted state before the step of removing the protective liner.

According to still another aspect, at least a portion of the substrate may include an adhesive material. The adhesive material may be provided on the substrate, and the protective liner may attach to the adhesive material. The tissue implant may be an engineered tissue, and the tissue implant may be placed on a surface of the substrate or be embedded in the substrate in a form of a cellular suspension. The substrate may be a bio-absorbable gel.

According to yet another aspect, the method may include attaching a carrier to the substrate on a surface opposite to the surface facing the lesion and removing the carrier from the substrate after the tissue implant is placed in the lesion. The method may also include forming the tissue patch into a contracted state, which may include folding the tissue patch or rolling the tissue patch into a cylindrical shape.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1A:
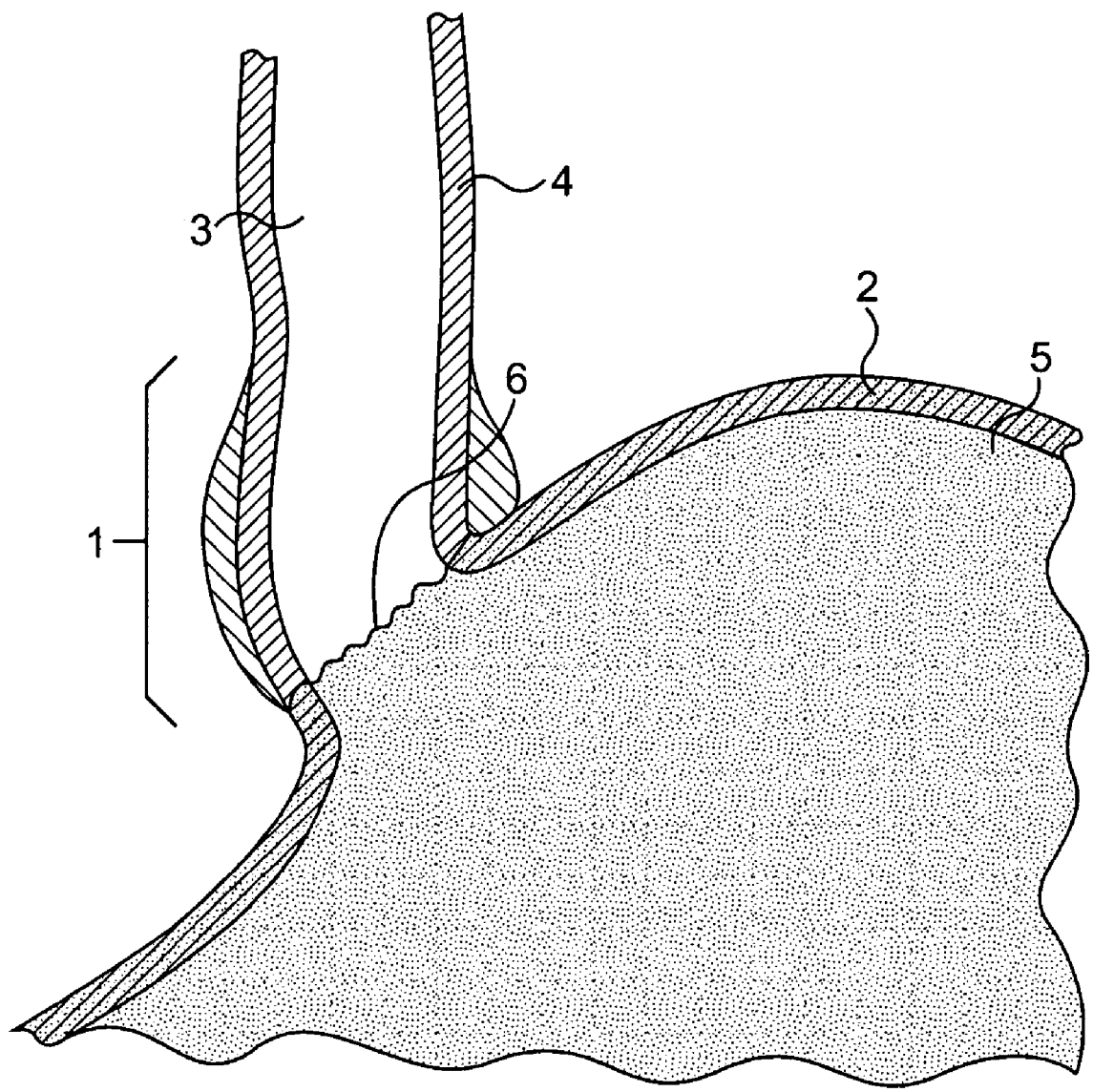
FIG. 1A is a schematic cross-sectional illustration of a healthy esophagus in the region of the lower esophageal sphincter (LES)
Figure 1B:
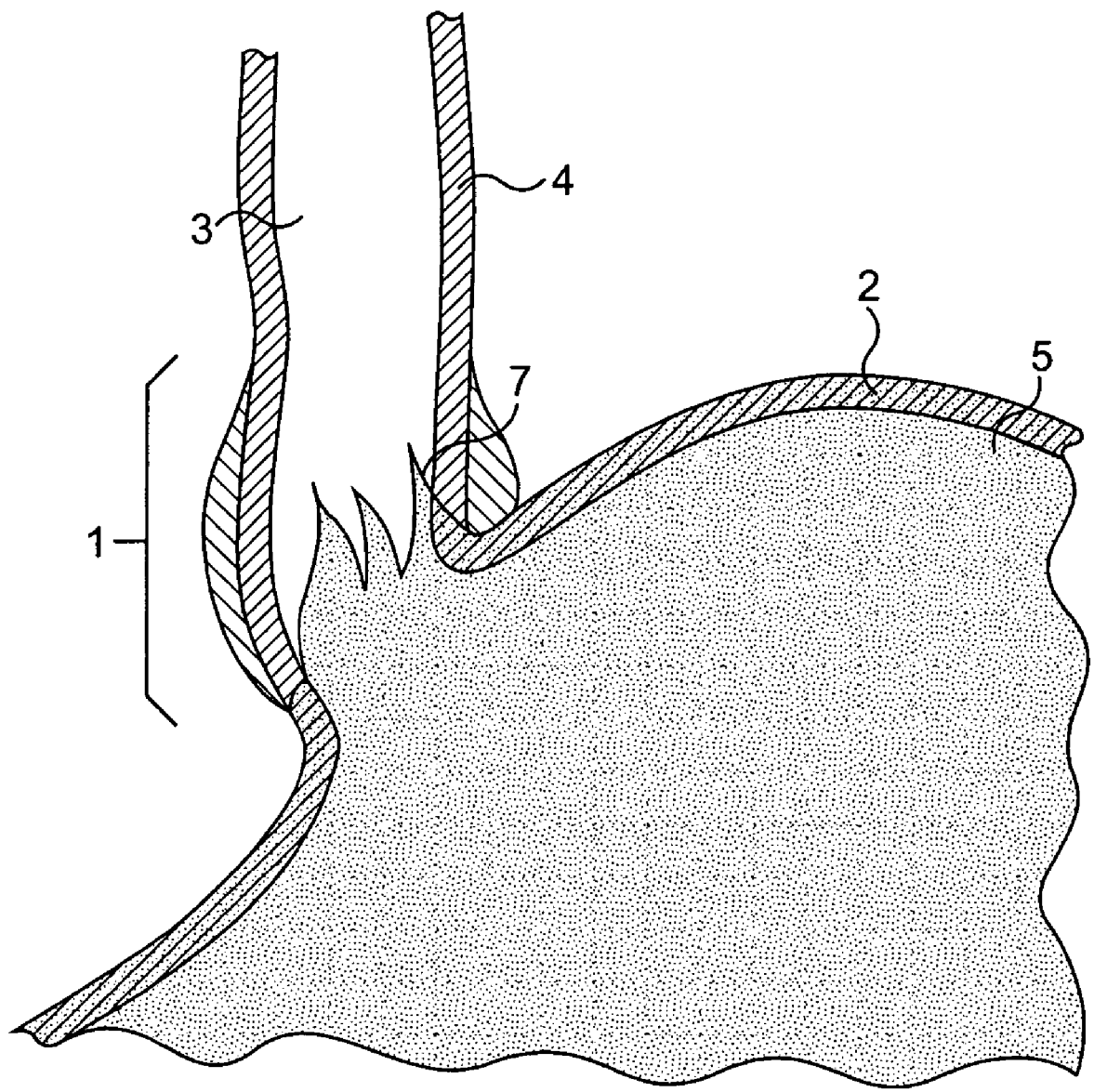
FIG. 1B is a schematic cross-sectional illustration of an esophagus with a pathological condition known as "Barrett's Esophagus" in the region of the lower esophageal sphincter (LES)
Figure 2:
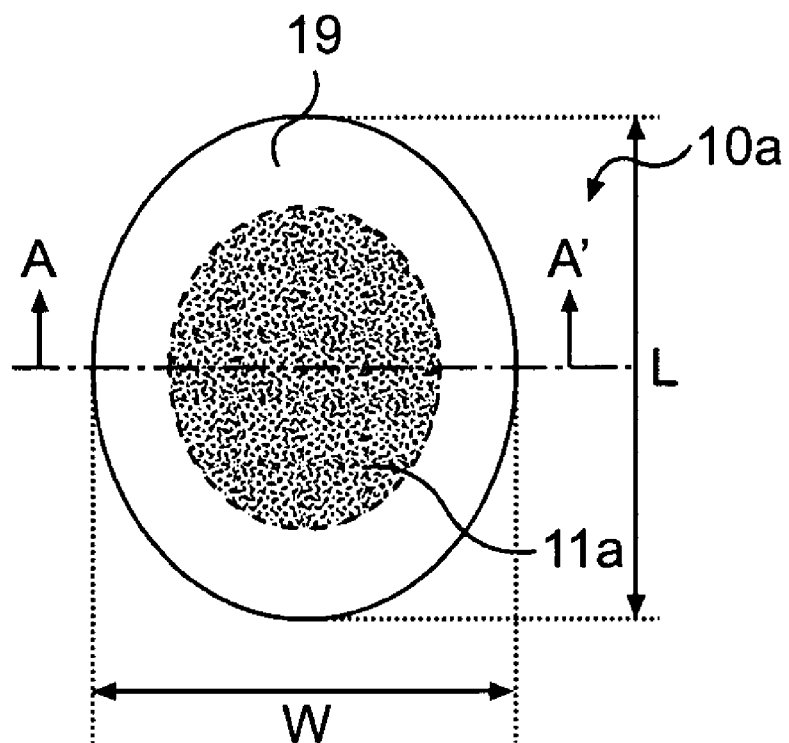
FIG. 2 is a top view of a tissue patch according to an embodiment of the present invention.
Figure 2A:
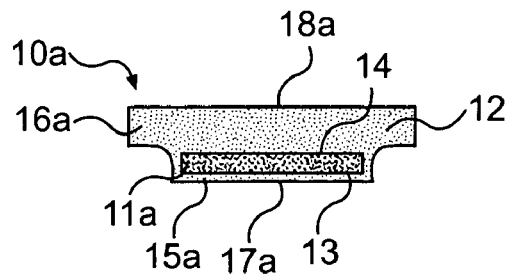
FIG. 2A is a cross-sectional side view of the tissue patch shown in FIG. 2 along the A-A' plane.

FIGS. 2 and 2A show top and cross-sectional (A-A') views of a tissue patch 10a according to an embodiment of the present invention. Referring to the figures, the tissue patch 10a may include a sheet of tissue implant 11a, preferably an engineered tissue (e.g., cultured tissue), embedded in a substrate, such as, for example, bio-absorbable gel 12, which can be dissolved in a patient's body over a period of time. The bottom surface 17a of the tissue patch 10a may be configured to contact the lesion to be treated while the top surface 18a may face a lumen of, for example, the alimentary tract of a patient. The bio-absorbable gel 12 forms a top layer 16a on the top surface 14 of the sheet of engineered tissue 11a and a bottom layer 15a on the bottom surface 13 of the sheet of engineered tissue 11a. The bio-absorbable gel layers 15a, 16a are intended to protect the tissue implant 11a from the harsh conditions in the lumen of the alimentary tract. In particular, the top layer 16a may have a predetermined thickness which may be greater than a predetermined thickness of the bottom layer 15a. This is because the top layer 16a is intended to protect the tissue implant during the time period required for healing of the lesion (for example, several days), while the bottom layer 15a is intended to protect the tissue only during insertion and placement of the patch 10a in the area of the lesion and quickly dissolve away, allowing layer 11a to stimulate growth of healthy tissue.

The area covered by the bio-absorbable gel 12 may be larger than the surface area of the sheet of tissue 11a, such that the area of the gel 12 containing no tissue forms a circumferential extension 19 to more effectively cover the area of the lesion. The area of circumferential extension 19 may be provided with bio-adhesive material to enhance attachment of the tissue patch to the lesion. It should be understood, however, that the bio-adhesive material may be applied to areas other than the circumferential extension 19 by coating or mixing in the bio-absorbable gel 12. It should also be understood that the tissue patch may be provided without the circumferential extension 19, as shown in FIGS. 3, 3A, and 3B.

Figure 2B:
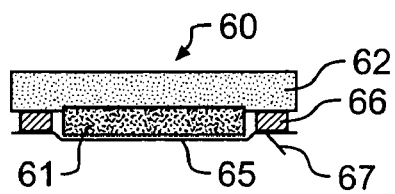
FIG. 2B is a cross-sectional side view of a tissue patch having a removable liner according to another embodiment of the present invention.

FIG. 2B shows a cross-sectional view of a tissue patch 60 having a removable layer or liner 65, according to another embodiment of the present invention. In this embodiment, a tissue patch 60 may be provided with a removable liner 65 to protect the sheet of engineered tissue 61 during its delivery to a desired endoluminal site. To attach the removable liner 65, a bio-adhesive material 66 may be applied in the circumferential area of the patch 60, preferably an area containing no tissue 61. The bio-adhesive material 66 then provides a bond between the removable liner 65 and the bio-absorbable material 62, thereby enclosing the engineered tissue 61 therein. While the removable liner 65 may have any desired shape, the liner 65 preferably has the same shape as that of the tissue patch 60. Optionally, the removable liner 65 may include a tab or a flap 67 formed, preferably, on a side edge of the liner 65 for enhanced gripping of the liner 65 during the removal process. When the liner 65 is removed, at least a portion of the bio-adhesive material 66 may remain on the bio-absorbable material 62 and serve to hold the tissue patch 60 in place over the lesion being treated. In an embodiment, the bio-adhesive material 66 may optionally or alternatively be applied to areas other than the circumferential area of the patch 60 by coating on or mixing with the bio-absorbable gel 62 or the engineered tissue 61. For example, if the sheet of tissue 61 covers substantially the entire surface of the bio-absorbable material 62 such that the tissue patch forms no circumferential extension, as shown in FIG. 3, the bio-adhesive material 66 may be coated on or mixed with the bio-absorbable gel 62 to attach the liner 65 thereon, as shown in FIG. 3B.

The bio-absorbable gel 12, 62 may be cross-linked polymer networks that can be manufactured to be responsive to temperature, light, pH, and/or a number of other internal/external stimuli. The gel response to external stimuli can take the form of variable viscosity, opacity, water absorption, permeability, and more. The bio-absorbable gel 12, 62 may comprise polylactic and/or polyglycolic polymers. The bio-absorbable gel 12, 62 may be infused with a number of therapeutic chemistries such as Human Growth Hormone (HGH), genetically engineered cells, antibiotics, analgesics or anaesthetics, and/or pH sensitive or reactive chemistry to promote cell growth in the tissue patch and the surrounding esophageal tissue, to relieve pain, prevent infection and hasten the healing process.

Figure 3:
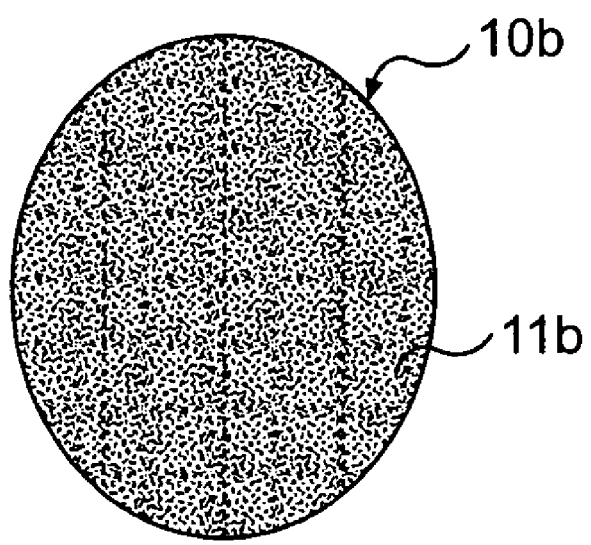
FIG. 3 is a top view of a tissue patch according to another embodiment of the present invention.
Figure 3A:
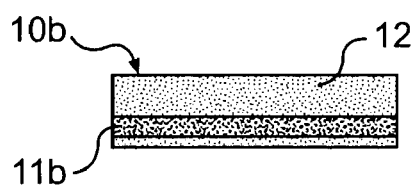
FIG. 3A is a cross-sectional side view of the tissue patch shown in FIG. 3.
Figure 3B:
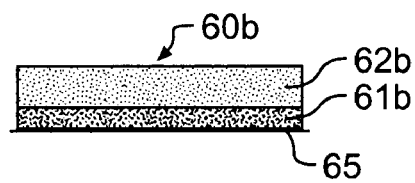
FIG. 3B is a cross-sectional side view of a tissue patch having a removable liner according to another embodiment of the present invention.
Figure 4A:
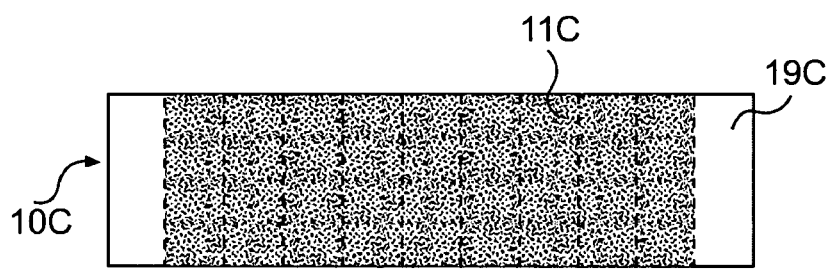
FIG. 4A is top and cross-sectional side views of a tissue patch according to yet another embodiment of the present invention.
Figure 4A:
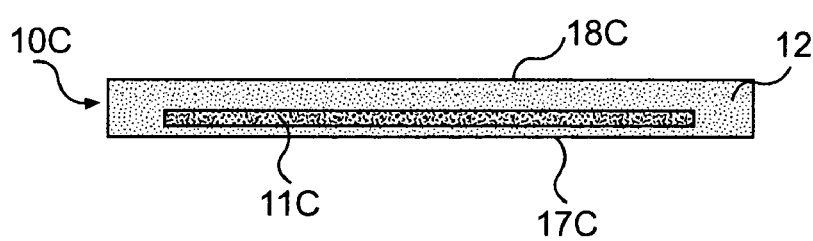
Figure 4B:
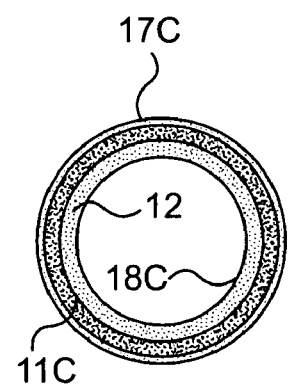
FIG. 4B is a cross-sectional elevation view of a cylindrical tissue path formed by curling the rectangular tissue patch shown in FIG. 4A outward according to still another embodiment of the present invention.

In the exemplary embodiments shown in FIGS. 2 and 3, the tissue patches 10a, 10b, 60 are shown to have an oval shape having a length L and a width W. It should be understood, however, that those patches 10a, 10b, 60 could, and most likely would, come in a variety of shapes and sizes depending upon the size and shape of the lesion to be treated. For example, as shown in FIG. 4A, a tissue patch 10c may be made rectangular. The rectangular tissue patch 10c may be curled outward to form a cylindrical patch used for treatment of a long circumferential lesion in a lumen, as shown in FIG. 4B.

As will be described later in detail, the tissue patches 10a, 10b, 10c, 60 shown in FIGS. 2, 3, 4A, and 4B may be configured to be folded into a compact form for an endoluminal deployment onto the site to be treated. In that case, the patches may be folded, for example, along dotted lines shown in FIGS. 3 and 4A or rolled into a cylindrical shape or any other columnar shape. The folded or rolled tissue patches 10a, 10b, 10c, 60 may form a similar shape shown in FIGS. 6A-6D, and may directly be delivered to a desired endoluminal treatment site by a suitable endoscopic device. When a tissue patch 60 having a removable liner 65 is used, a suitable grasping device (not shown) may be utilized to grasp and peal off the removable liner 65 once the tissue patch 60 is positioned proximate the lesion to be treated and ready to be placed in the lesion.

Figure 5A:
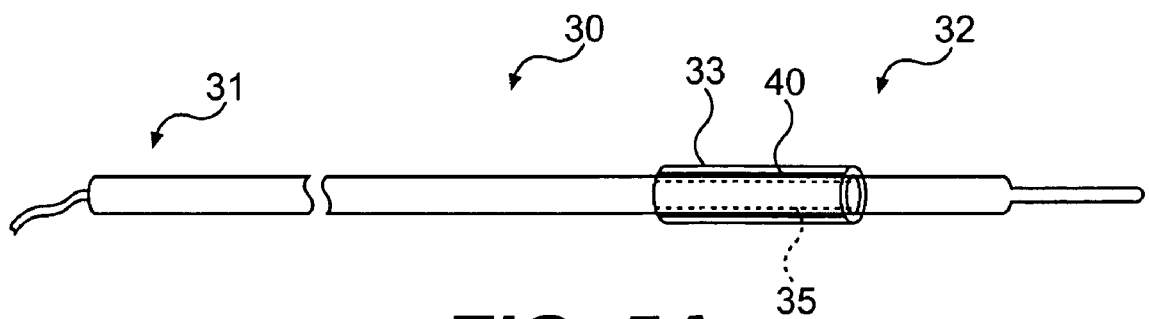
FIG. 5A is a delivery system for endoluminal delivery of a tissue implant, with an expandable member in a deflated state according to an embodiment of the present invention.
Figure 5B:
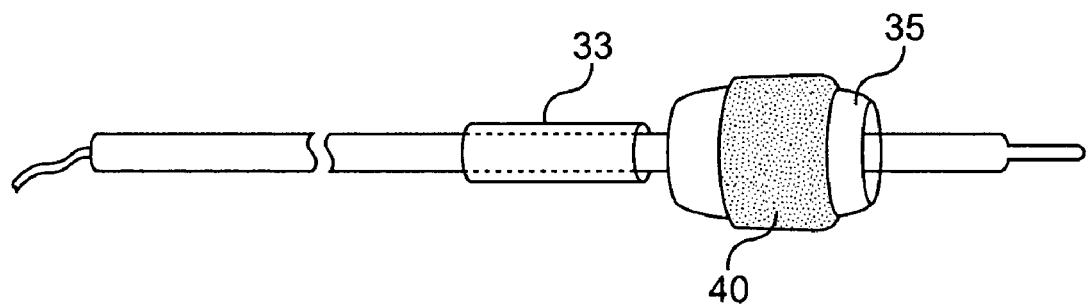
FIG. 5B is a delivery system for endoluminal delivery of a tissue implant, with an expandable member in an inflated state according to an embodiment of the present invention.

Another object of the present invention is to accurately deliver and attach the tissue implant endoluminally in situ. FIGS. 5A and 5B show a delivery system that may be used for delivering a tissue implant and associated materials endoluminally to a lesion to be treated. The delivery system may comprise a catheter 30 having a proximal portion 31 and a distal portion 32. An expandable member 35 may be located at the distal portion 32 of the catheter 30 and may be configured to expand upon actuation by a suitable actuator (not shown) at the proximal end of catheter 30. The catheter 30 may form a circumferential recess (not shown) in the distal portion 32 for receiving the expandable member 35 therein. This circumferential recess may have sufficient width and depth for accommodating the expandable member 35, so that the catheter 30 may have a substantially uniform outer surface when the expandable member 35 in its deflated state is positioned in the circumferential recess of the catheter 30. Although the expandable member 35 in this exemplary embodiment is a balloon 35, it should be understood that the expandable member 35 may be any other conventionally known expanding device. In the deflated state shown in FIG. 5A, the outer diameter of the expandable member 35 is essentially the same size as the catheter 30. The balloon 35 may be inflated pneumatically or hydraulically from an external source, such as a syringe, to expand to a predetermined diameter, as shown in FIG. 5B.

Figure 6:
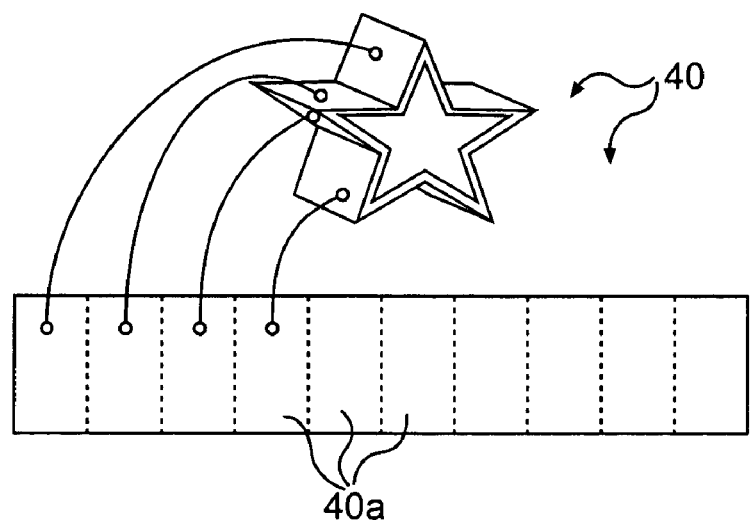
FIG. 6 is a carrier showing a folded state (top) and an unfolded state (bottom) according to an embodiment of the present invention.
Figure 6A:
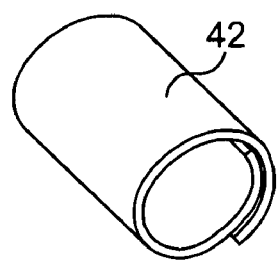
FIGS. 6A-D are expandable carriers showing a partially expanded state according to another embodiment of the present invention.
Figure 6B:
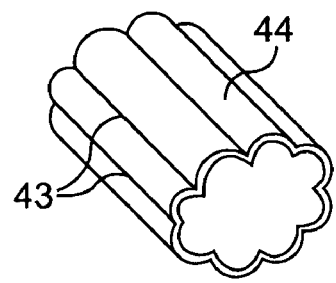
Figure 6C:
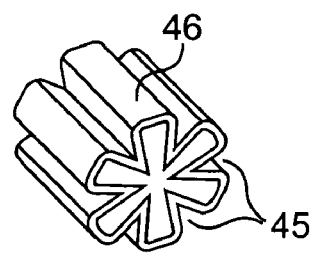
Figure 6D:
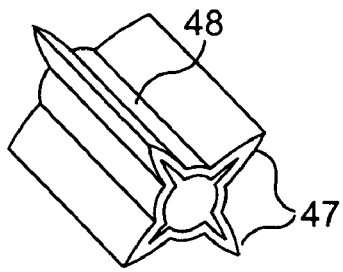

On the outer surface of the expandable member 35, a carrier 40 may be placed. In an embodiment, the carrier 40 may comprise a plurality of sections 40a or panels, which are capable of contracting into a compact form. For example, the carrier 40, in an unfolded, relaxed state, may form the shape of a star as shown in FIG. 6. Depending on the number of sections 40a, the carrier 40 may assume other shapes. The carrier, for example, may assume any suitable unfolded, relaxed state so long as the carrier may be contracted, folded, or otherwise take a suitable form or shape for delivery to the treatment site, and be capable of expanding, enlarging, unfolding, or otherwise taking a suitable form or shape for implantation at the treatment site. For example, in an alternative embodiment, the carrier may be a rectangular sheet 42 having its ends curled inwardly to form a substantially cylindrical tube, as shown in FIG. 6A. The ends of the sheet 42 may be slidable relative to each other, so as to contract or expand the cylindrical tube radially. In other alternative embodiments, the carrier may be a radially expandable tube 44, 46, 48 of any desired shape, as shown in FIGS. 6B-6D. In these embodiments, the expandable tube 44, 46, 48 may include at least one foldable portion 43, 45, 47 for facilitating the radial expansion of the tube 44, 46, 48.

Figure 7A:
FIGS. 7A-C are cross-sectional side views of a carrier holding a tissue implant according to various embodiments of the present invention.
Figure 7B:
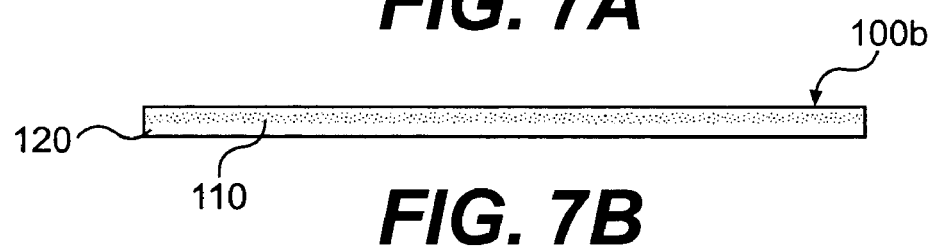
Figure 7C:
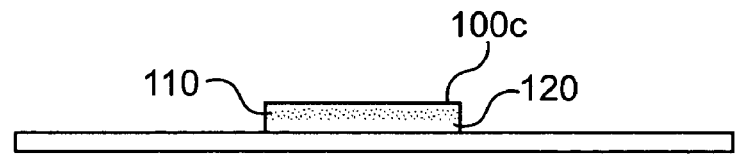

The carrier 40, 42, 44, 46, 48 can be configured to hold the tissue implant in various ways. For example, FIGS. 7A-7C show cross-sectional views of a carrier holding a tissue implant 110 according to various embodiments of the present invention. The tissue implant 110 embedded in a substrate 120, such as, for example, a bio-absorbable gel, and forming a patch 100a may be placed on the outer surface of the carrier 40 as shown in FIG. 7A. Also, the carrier 40 may itself constitute a substrate 120 and contain a tissue implant 110, shown FIG. 7B, so as to form a patch 100b. It should be understood that the size of the tissue implant 110 and/or the patch 100c may vary depending upon the size and location of the lesion to be treated, as shown in FIG. 7C.

Figure 8A:
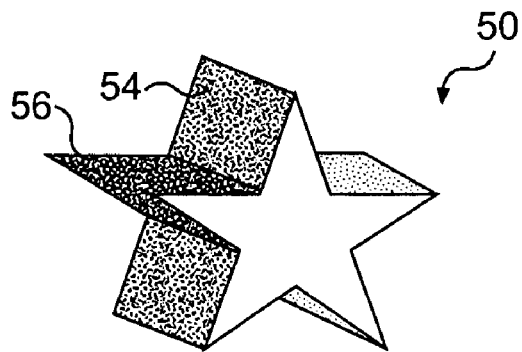
FIG. 8A is a carrier showing a folded state according to another embodiment of the present invention.
Figure 8B:
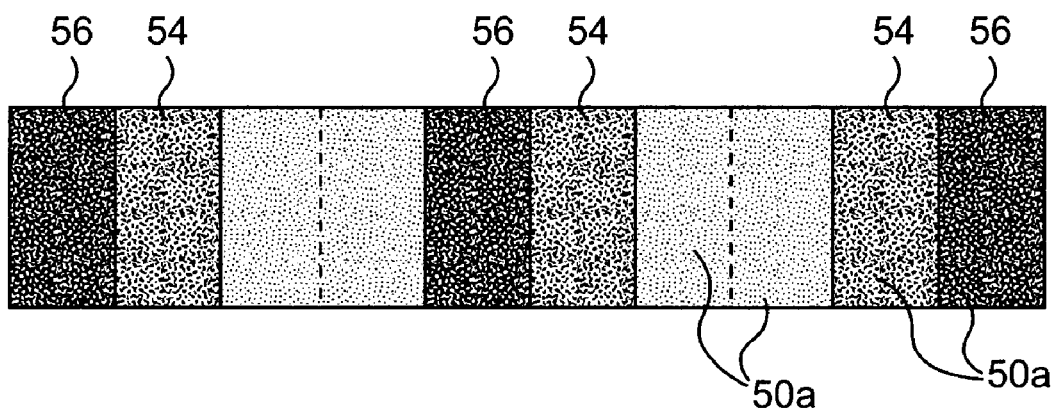
FIG. 8B is a carrier showing an unfolded state according to another embodiment of the present invention.
Figure 8C:
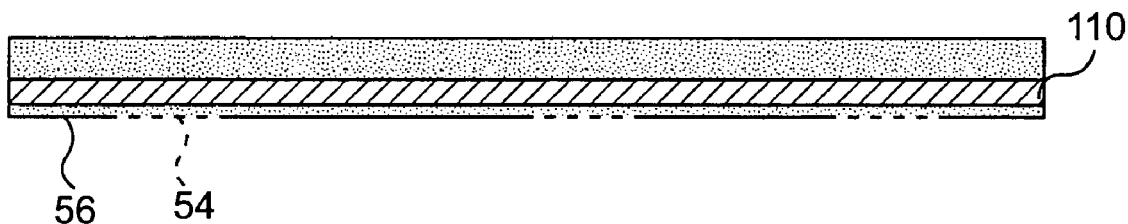
FIG. 8C is a cross-sectional side view of the carrier shown in FIG. 5B, showing the arrangement of the sections according to an embodiment of the present invention.

Another embodiment of the carrier 50 according to the present invention is shown in FIGS. 8A, 8B, and 8C. In this embodiment, the carrier 50 itself forms a tissue patch comprised of a plurality of sections 50a or panels, similar to the embodiment shown in FIG. 7B. The carrier 50 may form into any shape other than a star shown in FIG. 8A, similar to the possible variations illustrated above with respect to the exemplary embodiments of FIGS. 6 and 6A-D.

Some of the sections 50a may be coated with bio-adhesive material 54 that will hold the carrier 50 and the tissue implant 110 in contact with the lesion. When the sections 50a are coated with bio-adhesive material 54, the sections 50a may be arranged in such a way that when the carrier 50 is folded, those sections 50a holding the tissue implant contact like sections and those sections coated with bio-adhesive material 54 will be in contact with a non-stick material 56, preserving the ability to release during deployment. Similar arrangement is possible for the carriers shown in FIGS. 6A-D.

Various materials, such as, for example, PTFE or any suitable bio-absorbable material, can be utilized to form the carrier 40. In the case where the carrier 40 is used to place a tissue patch 100a (e.g., as shown in FIG. 7A) on the outer surface of the carrier 40, the carrier 40 can be formed of a separable layer that can be peeled away once the materials in the tissue patch 100a are securely implanted. On the other hand, in case where the carrier 40 itself forms a tissue patch (e.g. as shown in FIG. 7B), the substrate 120 may be formed of any of a number of bio-degradable materials, such as polylactic acid (PLA), which dissolves in vivo over a period of time, leaving only the implanted materials. As discussed above, selection of material and/or composition and physical structure of the substrate 120 may depend on estimated degradation time of the substrate material. This estimated degradation time may correspond to the time period necessary for the implanted tissues to establish themselves. The substrate 120 may also encompass various therapeutic agents to promote healing process as well as bio-adhesive material to enhance attachment of the tissue implant to the lesion.

The delivery system may further comprise a retractable sleeve 33 surrounding the carrier 40 and the tissue implant 110 to protect the tissue implant 110 and other associated materials during insertion and placement of the catheter 30 at a lesion to be treated. The sleeve 33 may be configured to retract from around the carrier 40 prior to the expandable member 35 expanding to the expanded state, as illustrated in FIG. 5B.

Figure 10:
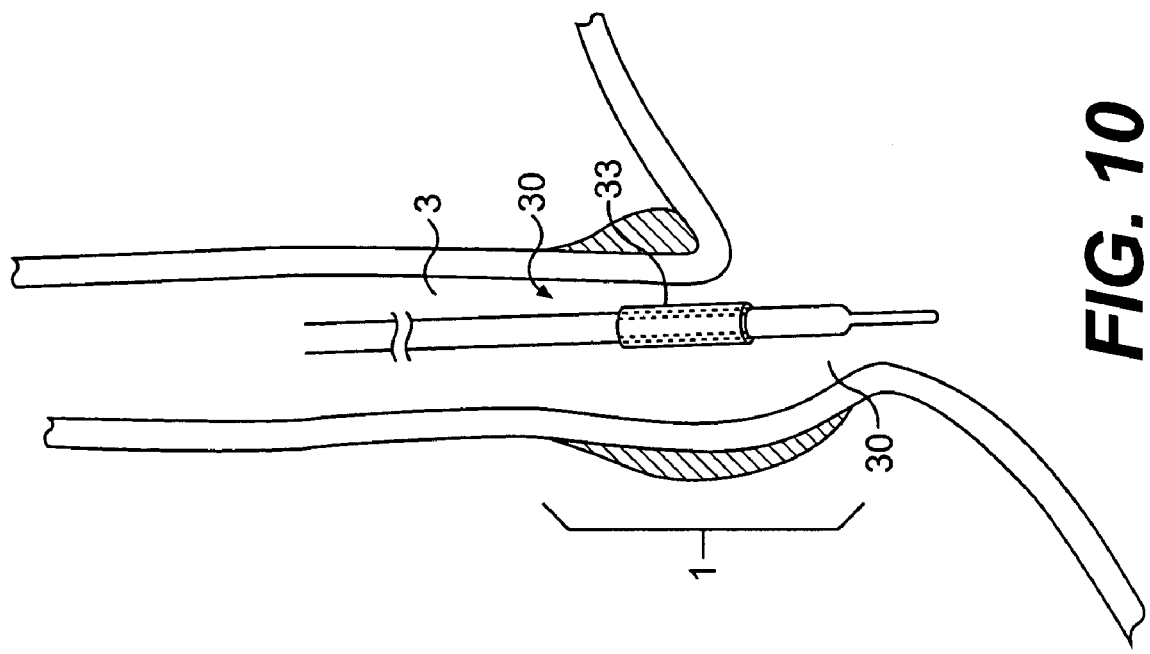
FIG. 10 is a schematic illustration of a tissue delivery system with an expandable member deflated in position for deployment in the esophagus.
Figure 9:
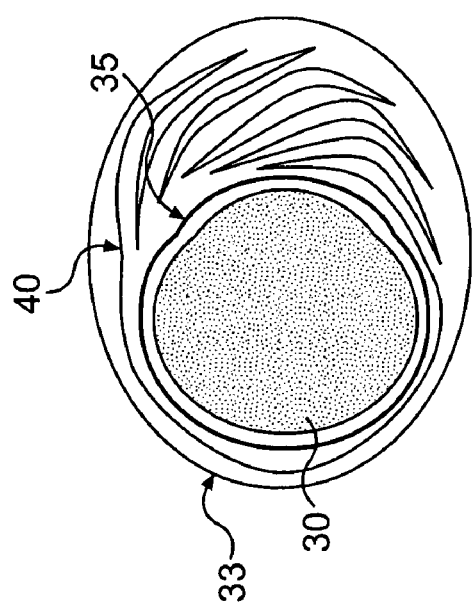
FIG. 9 is a cross-sectional view of a delivery system including a catheter, an expandable member, a carrier, and a sleeve, with the expandable member in a deflated state according to an embodiment of the present invention.

As an exemplary embodiment, application of engineered tissue and associated materials to the lower esophagus in the treatment of GERD or other disorders is described with respect to FIGS. 9 and 10. The specific embodiment of the present invention comprises a method for delivering an engineered tissue implant and associated materials endoluminally to a circumferential area near the lower esophageal junction.

FIG. 9 shows a cross-sectional view of a delivery system with an expandable member, e.g., a balloon 35, in deflated state during the insertion. The carrier 40 may be tightly folded and contained in a sleeve 33 to maintain a small diameter and protect the tissue implant and other associated materials, as shown in FIG. 9. The materials on the sections of the carrier 40 may be arranged to prevent cross-contamination and to facilitate deployment. The tissue implant may be arranged in such a way that, when the carrier is folded, sections with the tissue implant can contact with like sections and sections that are in contact with the bio-adhesive material are coated with a non-stick gel.

FIG. 10 shows the delivery system in position for deployment in the lesion of esophagus. The delivery system may include an endoscope to visualize the delivery process along the passageway to the lesion of esophagus. Other suitable methods of visualization, including fluoroscopy, may be used. Once the delivery system is in position, the sleeve 33 can be retracted or removed from around the expandable member 35, and the carrier 40 can be uncovered to expose the carrier 40 and the tissue implant 110. Any conventional method known in the art may be utilized to retract or remove the sleeve 33. For example, the sleeve 33 may be configured to slide down or split open to expose the carrier 40 when the balloon is inflated, or may be retracted using endoscopy instruments. The sleeve 33 may be constructed of a biodegradable material that would dissolve away. Alternatively, the sleeve 33 may be made of any material that can safely pass through the digestive tract.

Figure 11A:
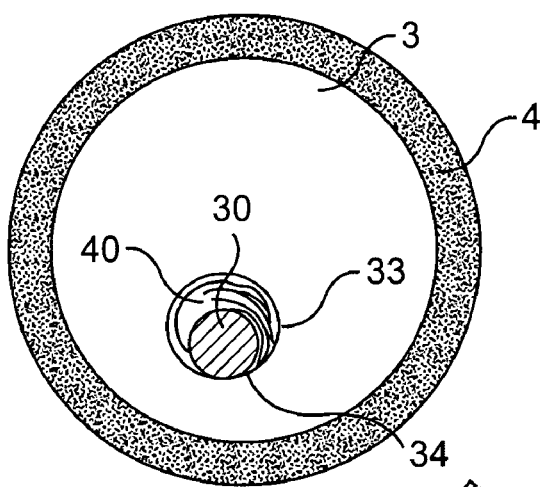
FIGS. 11A-C are cross-sectional views through a region of an esophagus showing the delivery system in three stages of inflation within the esophagus according to an embodiment of the present invention.
Figure 11B:
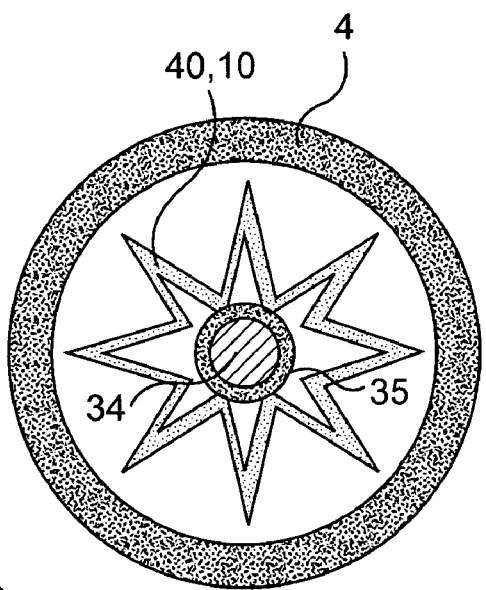
Figure 11C:
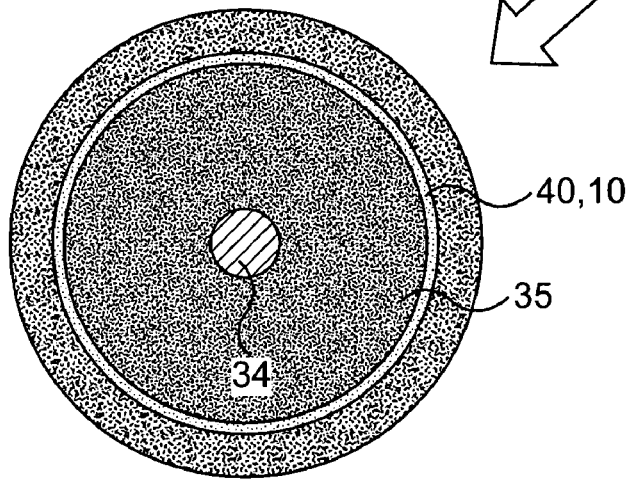

FIGS. 11A-11C show the cross-sectional views of the expandable member in exemplary, representative stages of inflation within the esophagus 3, illustrating various stages of the delivery process. For illustration purposes only, the delivery process is illustrated with respect to the exemplary carrier 40 shown in FIG. 6. Substantially identical steps or processes can be used for the carriers 42, 44, 46, 48 shown in FIGS. 6A-6D or any other suitable carrier. First, the delivery system is shown with the sleeve 33 in place and the balloon 35 deflated, as shown in FIG. 11A. Next, the sleeve 33 is retracted or removed, and the balloon 35 is partially inflated, allowing the carrier 40 to expand into its intermediate shape, shown in FIG. 11B. The carrier 40 may be formed of a material that has a characteristic of returning to its natural shape, shown in FIG. 11B. Finally, the configuration at full inflation of balloon 35 is shown in FIG. 11C. The carrier 40 may then have an intimate contact with the lining of the esophagus 3 and, by the use of bio-adhesive material or any other suitable mechanism, the carrier 40 and the tissue implant 10 may be fixed in place. In an alternative embodiment, the carrier 40 may be expanded into its fully expanded position without the intermediate step of partially inflating the carrier 40.

The carrier 40 may also include an optional radially expanding device, such as a stent, to provide additional force against the esophageal wall. If a radially expanding device is used, the device may be removed after a predetermined time period. Alternatively, the device made be made of a bio-absorbable material such that it can be dissolve away after a prescribed time period.

Once the tissue implant 10 is fixed in place, the balloon 35 can be deflated, leaving the carrier 40 and implant materials 10 fixed to the luminal wall 4. The choice of carrier substrate material will determine whether further intervention will be necessary to remove the leftover substrate material, once the cell colonies are established.

According to another exemplary embodiment, if a tissue implant is to be attached to a relatively small lesion, a smaller tissue patch, such as, for example, the tissue patches shown in FIGS. 2 and 3, can be used. A smaller tissue patch can be placed on a portion of the carrier 40 or expandable member 35 for delivery. An adhesive sheet, a stent, a grasper, or any other suitable mechanism can optionally be used to facilitate accurate delivery of the tissue patch. The remaining steps of delivery are substantially identical to the steps described above.

Figure 12:
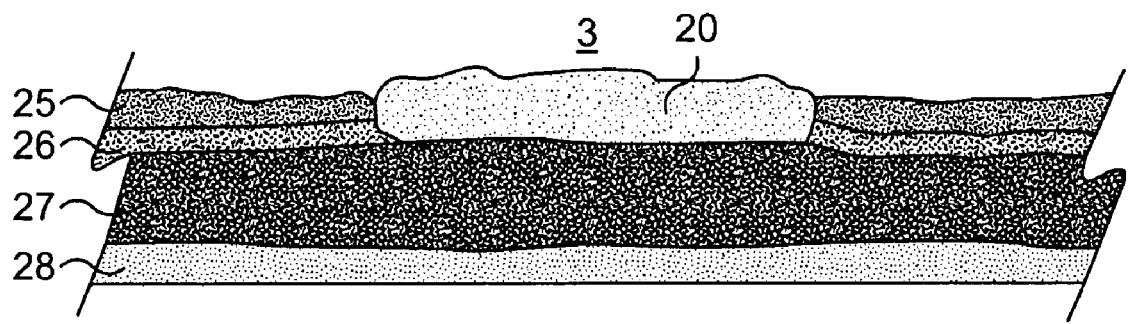
FIG. 12 is a cross-sectional view through a region of an esophagus having a diseased tissue before a resection of the diseased tissue is performed.
Figure 13:
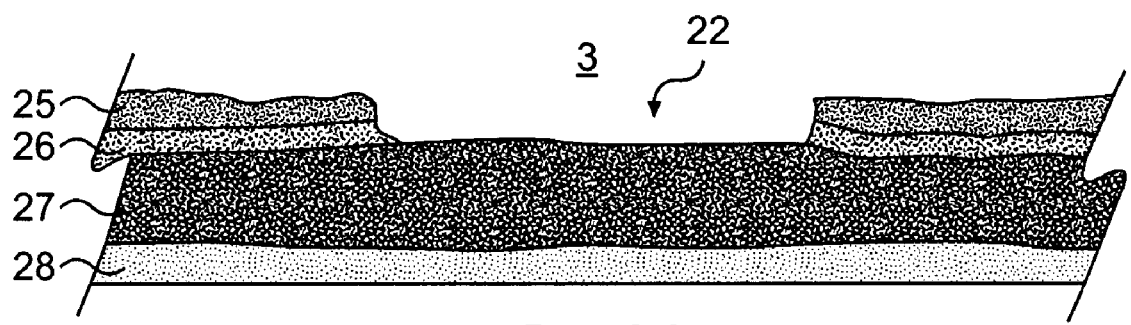
FIG. 13 is a cross-sectional view through a region of an esophagus after a resection of the diseased tissue is performed.

For the purpose of explaining a function of the tissue patches 10, a cross-section through a region of the esophagus containing abnormal epithelium 20, e.g., Barrett's Epithelium, is shown in FIG. 12. It is often necessary to surgically remove the diseased tissue 20. However, after a resection of the diseased tissue 20 has been performed, a large opening 22 is left in the esophagus 3. For illustration purposes only, it is assumed that the disease (e.g., abnormal epithelium 20) affected the mucosa layer 25 and submucosa layer 26, as shown in FIG. 13. In this condition, the muscularis layer 27 above the serosa layer 28 of the esophagus 3 is exposed to the harsh environment of the lower esophagus 21.

Figure 14:
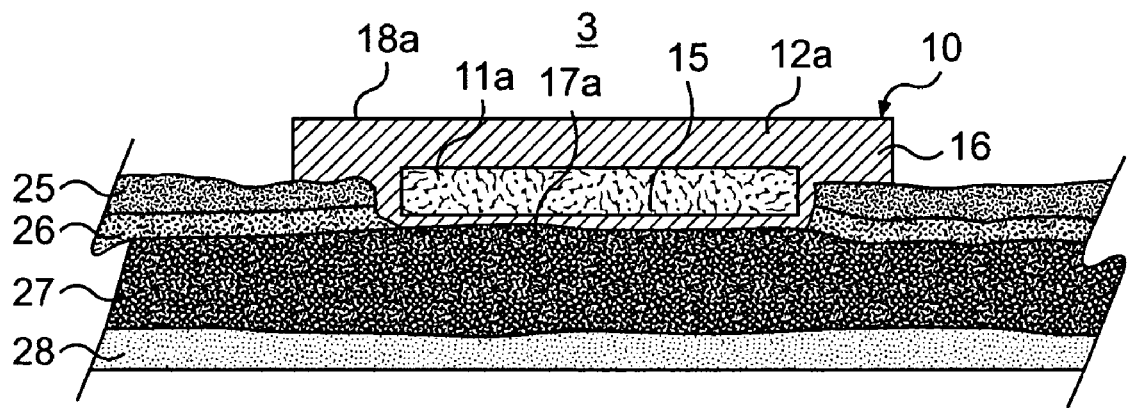
FIG. 14 is a cross-sectional view through a region of an esophagus after a tissue patch is delivered to the resection site, according to an embodiment of the present invention.

FIG. 14 shows how the endoluminal tissue patch 10 of the present invention, delivered to the site 22 endoluminally through an overtube or endoscope, would be used to fill and protect the region of exposed muscularis layer 27. The bottom surface 17a of the tissue patch may be placed in contact with the muscularis layer 27 while the top surface 18a faces toward the lumen of the esophagus 3. The bio-absorbable gel layer 16 that covers the top of the tissue implant can be made thicker to ensure that it will last, for example, several days, serving to protect the tissue implant 11a from the harsh chemistry of the lower esophagus 3. The thinner bio-absorbable gel layer 15 on the bottom surface of the tissue implant 11a may only last long enough to protect the tissue implant 11 during its deployment to the treatment site 22. In addition, the bio-absorbable gel 12 could be infused with any of a number of therapeutic agents, such as, for example, Human Growth Hormone (HGH), genetically engineered cells, antibiotics, analgesics or anaesthetics, and/or pH sensitive or reactive chemistry. Over time, as the bio-absorbable gel is absorbed, these chemistries would be released into the site, promoting cell growth in the tissue patch and the surrounding esophageal tissue, relieving pain, preventing infection, and hastening the healing process.

Figure 15A:
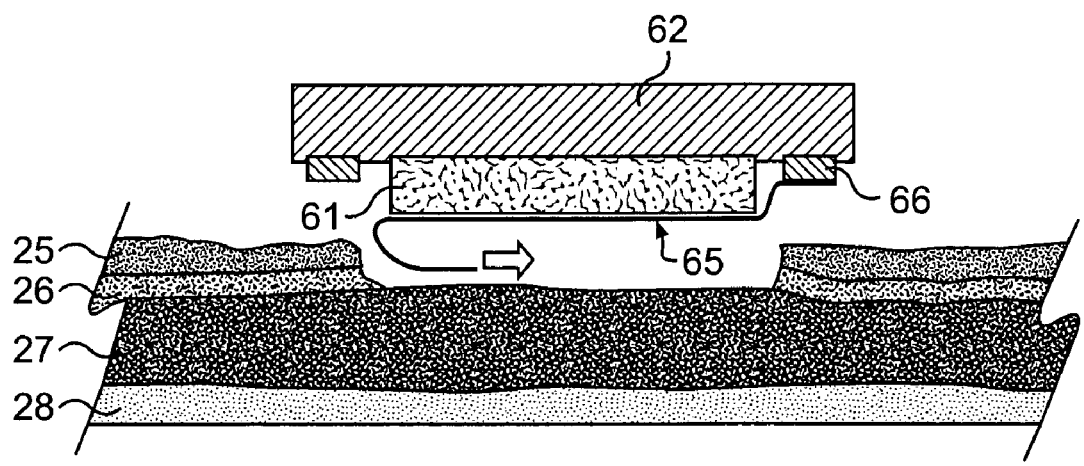
FIG. 15A is a cross-sectional view through a region of an esophagus, illustrating removal of a removable liner prior to delivery of a tissue patch onto the resection site, according to another embodiment of the present invention.
Figure 15B:
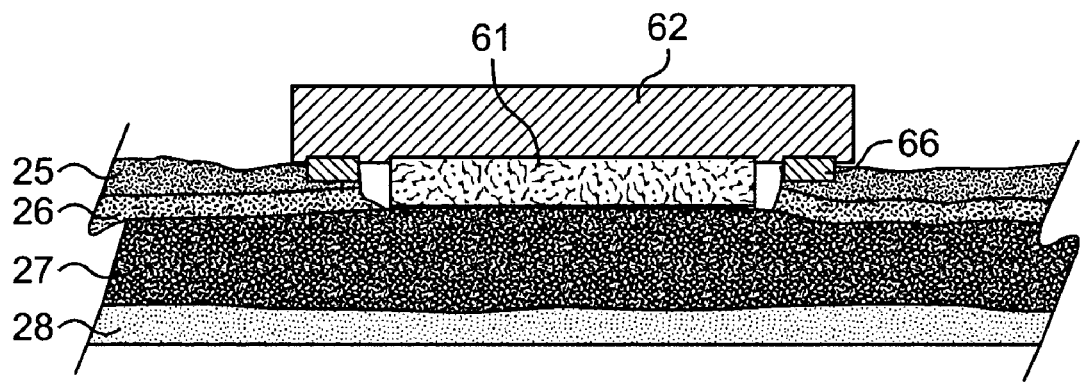
FIG. 15B is a cross-sectional view through a region of an esophagus after the tissue patch of FIG. 15A is delivered to the resection site, according to another embodiment of the present invention.

When a tissue patch 60 having a removable liner 65 (e.g., shown in FIGS. 2B and 3B) is used, the removable liner 65 may be peeled away before placing this tissue patch 60 over the site, as shown in FIG. 15A. Once the liner 65 is removed and the engineered tissue 61 is exposed, the tissue patch 60 is placed over the region of exposed muscularis layer 27. The engineered tissue 61 then may directly contact the muscularis layer 27, as shown in FIG. 15B. The bio-adhesive material 66 is then brought into contact with the healthy tissue surrounding the opening, holding the tissue patch 60 in place.

Figure 16:
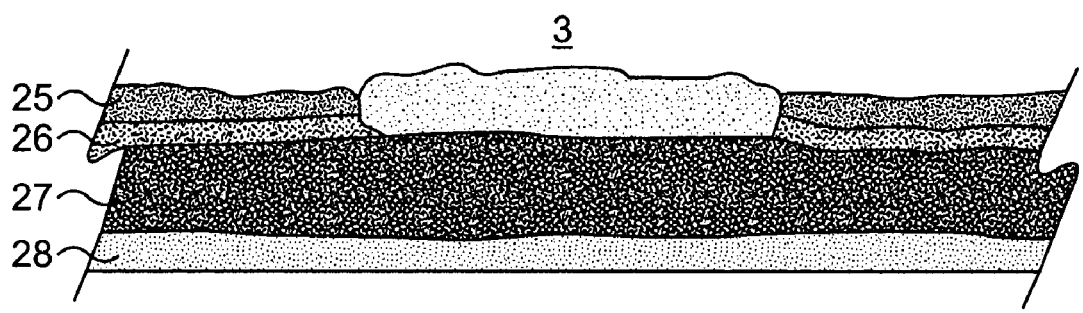
FIG. 16 is a cross-sectional view through a region of an esophagus showing a fully healed site.

FIG. 16 illustrates the fully healed site. The therapeutic agents referred to above may be provided in layers such that each of the chemical agents can be activated at a predetermined time during the treatment process in a controlled manner.

Although the present invention is depicted in this disclosure as being used in the treatment of wounds in the esophagus of a patient with Barrett's Esophagus, it is understood that the endoluminal delivery and the tissue patches according to the present invention could be used to treat any of a number of different disease conditions in the alimentary tract. Examples of this would be in the treatment of gastric or duodenal ulcers or to promote healing at sites of surgical resection of gastrointestinal polyps or tumors. Furthermore, it is also to be understood that the tissue implant may be replaced with any other type of cells depending on its use, e.g., vascular endothelial cells such as xenografts, allografts, or autografts.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a lesion in a nonvascular lumen of patient's body, comprising:

providing a tissue patch having a tissue implant attached to a substrate and a protective liner covering at least a portion of the tissue implant;

forming the tissue patch into a contracted state;
inserting the tissue patch in the contracted state into a lumen containing the lesion;
positioning the tissue patch in the vicinity of the lesion;
removing the protective liner to reveal the tissue implant; and placing the tissue implant in the lesion.

2. A method according to claim 1, further comprising placing the tissue patch on a portion of a catheter for inserting the tissue patch in the contracted state.

3. A method according to claim 1, further comprising expanding the tissue patch from the contracted state before the step of removing the protective liner.

4. A method according to claim 1, wherein an adhesive material is provided on the substrate and the protective liner attaches to the adhesive material.

5. A method according to claim 1, wherein at least a portion of the substrate includes an adhesive material.

6. A method according to claim 1, wherein the tissue implant is placed on a surface of the substrate.

7. A method according to claim 1, wherein the tissue implant is embedded in the substrate in a form of a cellular suspension.

8. A method according to claim 1, wherein the substrate is a bio-absorbable gel.

9. A method according to claim 1, further comprising attaching a carrier to the substrate on a surface opposite to the surface facing the lesion and removing the carrier from the substrate after the tissue implant is placed in the lesion.

10. A method according to claim 1, wherein the tissue implant is an engineered tissue.

11. A method according to claim 1, wherein forming the tissue patch into a contracted state includes folding the tissue patch.

12. A method according to claim 1, wherein forming the tissue patch into a contracted state includes rolling the tissue patch into a cylindrical shape.

13. A method according to claim 1, wherein the implant of tissue comprises a sheet of tissue.

* * * * *